(12) United States Patent
Lee et al.

(10) Patent No.: US 10,959,770 B2
(45) Date of Patent: Mar. 30, 2021

(54) METHOD OF ASSEMBLING AN ELECTROSURGICAL INSTRUMENT

(71) Applicant: Covidien LP, Mansfield, MA (US)

(72) Inventors: Weng-Kai K. Lee, Longmont, CO (US); Scott N. Lacosta, Lafayette, CO (US); Kelley D. Goodman, Erie, CO (US); Keir Hart, Lafayette, CO (US); Duane E. Kerr, Loveland, CO (US); Geneva Ladtkow, Arvada, CO (US); Kenneth E. Netzel, Loveland, CO (US); Jeffrey R. Townsend, Longmont, CO (US); Raghavendra L. Bhandari, Karnataka (IN); Peixiong Yi, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 234 days.

(21) Appl. No.: 15/961,461

(22) Filed: Apr. 24, 2018

(65) Prior Publication Data
US 2018/0235690 A1    Aug. 23, 2018

Related U.S. Application Data

(63) Continuation of application No. 14/906,072, filed as application No. PCT/CN2013/080947 on Aug. 7, 2013, now Pat. No. 9,962,221.

(51) Int. Cl.
*A61B 18/14*    (2006.01)
*A61B 90/00*    (2016.01)
(Continued)

(52) U.S. Cl.
CPC .......... *A61B 18/1442* (2013.01); *A61B 90/03* (2016.02); *A61B 2018/00922* (2013.01);
(Continued)

(58) Field of Classification Search
CPC ...... A61B 18/1442; A61B 2018/00922; A61B 2018/00958; A61B 2018/126;
(Continued)

(56) References Cited

U.S. PATENT DOCUMENTS

D249,549 S    9/1978 Pike
D263,020 S    2/1982 Rau, III
(Continued)

FOREIGN PATENT DOCUMENTS

CN    201299462 Y    9/2009
CN    202086577 U    12/2011
(Continued)

OTHER PUBLICATIONS

Australian Examination Report No. 2 issued in Appl. No. AU 2017201241 dated Oct. 17, 2018 (4 pages).
(Continued)

*Primary Examiner* — Minh N Trinh

(57) ABSTRACT

A method of assembling an electrosurgical instrument includes coupling first and second shafts to each other about a pivot. Each of the shafts has an interior side facing the other shaft and an exterior side opposite the interior side. The method also includes disposing a knife blade at least partially through a passageway defined through the pivot from the exterior side of the first shaft and coupling a knife actuation mechanism to the first shaft from the exterior side of the first shaft. The knife actuation mechanism is configured to move the knife blade through the passageway.

12 Claims, 14 Drawing Sheets

(51) Int. Cl.
*A61B 18/00* (2006.01)
*A61B 18/12* (2006.01)

(52) U.S. Cl.
CPC ............... *A61B 2018/00958* (2013.01); *A61B 2018/126* (2013.01); *A61B 2018/1455* (2013.01); *A61B 2018/1495* (2013.01); *A61B 2090/034* (2016.02)

(58) Field of Classification Search
CPC .... A61B 2018/1455; A61B 2018/1495; A61B 2090/034; A61B 90/03
See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,100,420 A | 3/1992 | Green et al. |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,578,052 A | 11/1996 | Koros et al. |
| 5,618,294 A | 4/1997 | Aust et al. |
| D384,413 S | 9/1997 | Zlock et al. |
| 5,665,100 A | 9/1997 | Yoon |
| H1745 H | 8/1998 | Paraschac |
| 5,814,043 A | 9/1998 | Shapeton |
| D402,028 S | 12/1998 | Grimm et al. |
| D408,018 S | 4/1999 | McNaughton |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H1904 H | 10/2000 | Yates et al. |
| 6,277,117 B1 | 8/2001 | Tetzlaff et al. |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| 6,346,106 B1 | 2/2002 | Jako |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H2037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,673,092 B1 | 1/2004 | Bacher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| 7,922,718 B2 * | 4/2011 | Moses ............... A61B 18/1442 606/51 |
| 8,147,489 B2 | 4/2012 | Moses et al. |
| 8,298,233 B2 | 10/2012 | Mueller |
| 8,394,096 B2 | 3/2013 | Moses et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,685,009 B2 | 4/2014 | Chernov et al. |
| 8,685,021 B2 | 4/2014 | Chernov et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,852,185 B2 | 10/2014 | Twomey |
| 8,858,553 B2 | 10/2014 | Chojin |
| 8,888,771 B2 | 11/2014 | Twomey |
| 8,888,775 B2 | 11/2014 | Nau, Jr. et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |

(56) References Cited

U.S. PATENT DOCUMENTS

| | | |
|---|---|---|
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 9,844,384 B2 | 12/2017 | Chernov et al. |
| 9,962,221 B2 | 5/2018 | Lee et al. |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0208196 A1 | 11/2003 | Stone |
| 2003/0229344 A1 | 12/2003 | Dycus et al. |
| 2004/0092927 A1 | 5/2004 | Podhajsky et al. |
| 2005/0004559 A1 | 1/2005 | Quick |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0260241 A1 | 11/2007 | Dalla Betta et al. |
| 2008/0215048 A1 | 9/2008 | Hafner et al. |
| 2009/0082766 A1 | 3/2009 | Unger et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2010/0016857 A1 | 1/2010 | McKenna et al. |
| 2010/0130977 A1 | 5/2010 | Garrison et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083786 A1 | 4/2012 | Artale et al. |
| 2012/0083827 A1 | 4/2012 | Artale et al. |
| 2012/0123404 A1 | 5/2012 | Craig |
| 2012/0172868 A1 | 7/2012 | Twomey et al. |
| 2012/0172873 A1 | 7/2012 | Artale et al. |
| 2012/0184990 A1 | 7/2012 | Twomey |
| 2012/0239034 A1 | 9/2012 | Horner et al. |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0330308 A1 | 12/2012 | Joseph |
| 2013/0022495 A1 | 1/2013 | Allen, IV et al. |
| 2013/0041370 A1 | 2/2013 | Unger |
| 2013/0138101 A1 | 5/2013 | Kerr |
| 2016/0157925 A1 | 6/2016 | Artale et al. |
| 2018/0235590 A1* | 8/2018 | Smith ............... A61B 17/3423 |

FOREIGN PATENT DOCUMENTS

| | | |
|---|---|---|
| CN | 102525639 A | 7/2012 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 102004026179 A1 | 12/2005 |
| DE | 202007009165 U1 | 8/2007 |
| DE | 202007009317 U1 | 10/2007 |
| DE | 202007016233 U1 | 1/2008 |
| DE | 102008018406 B3 | 7/2009 |
| EP | 1159926 A2 | 3/2003 |
| EP | 2353535 A1 | 8/2011 |
| EP | 2436330 A1 | 4/2012 |
| JP | 61501068 | 9/1984 |
| JP | 6502328 | 3/1992 |
| JP | 55106 | 1/1993 |
| JP | 0540112 | 2/1993 |
| JP | 5121797 | 5/1994 |
| JP | 6285078 | 10/1994 |
| JP | 06343644 A | 12/1994 |
| JP | 6511401 | 12/1994 |
| JP | 07265328 A | 10/1995 |
| JP | 856955 | 3/1996 |
| JP | 08252263 A | 10/1996 |
| JP | 8317934 | 12/1996 |
| JP | 910223 | 1/1997 |
| JP | 9122138 | 5/1997 |
| JP | 1024051 | 1/1998 |
| JP | 10155798 | 6/1998 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000342599 A | 12/2000 |
| JP | 2000350732 A2 | 12/2000 |
| JP | 2001008944 | 1/2001 |
| JP | 2001029356 | 2/2001 |
| JP | 2001128990 A | 5/2001 |
| JP | 2001190564 A | 7/2001 |
| JP | 2004517668 A | 6/2004 |
| JP | 2004524124 A | 8/2004 |
| JP | 2004528869 A | 9/2004 |
| JP | 2005144193 A | 6/2005 |
| JP | 2012075906 A | 4/2012 |
| SU | 401367 A1 | 10/1973 |
| WO | 9400059 A1 | 1/1994 |
| WO | 9923933 A2 | 5/1999 |
| WO | 0024330 A1 | 5/2000 |
| WO | 0036986 A1 | 6/2000 |
| WO | 0115614 A1 | 3/2001 |
| WO | 0154604 A1 | 8/2001 |
| WO | 02080786 A1 | 10/2002 |
| WO | 02080793 A1 | 10/2002 |
| WO | 2005110264 A2 | 4/2006 |
| WO | 2013022928 A1 | 2/2013 |

OTHER PUBLICATIONS

Extended European Search Report issued in corresponding Appl. No. EP 182119255 dated Apr. 29, 2019 (7 pages).

Australian Examination Report issued in Appl. No. AU 2017201241 dated Jul. 20, 2018 (3 pages).

(56) References Cited

OTHER PUBLICATIONS

International Search Report and Written Opinion of the International Searching Authority dated Jan. 17, 2013 from counterpart International Application No. PCT/US20121050094 (8 pgs.).
European Search Report, dated Feb. 19, 2015, corresponding to European Patent Application No. 12824142.9; 6 pages.
European Extended Search Report dated Jun. 29, 2015, corresponding to European Application No. 12824142.9; 10 pages.
English translation of first Chinese Office Action and Search Report dated Aug. 28, 2015, corresponding to Chinese Patent Application No. 201280035427.4; 9 total pages.
International Search Report and Written Opinion of the International Searching Authority dated Apr. 29, 2014 from counterpart International Application No. PCT/CN2013/080947.
Australian Examiner's Report dated Jun. 6, 2016 issued in corresponding Australian Patent Application No. 2015243043.
Chinese Office Action and English language translation from Appl. No. CN 201410385523.2 dated Mar. 23, 2017.
Chinese Office Action and English language translation, issued in Appl. No. CN 201610177959.1 dated Apr. 19, 2017.
Extended European Search Report issued in Appl. No. EP 13891096.3 dated Jun. 22, 2017.
Partial European Search Report from Appl. No. EP 13891096.3 dated Mar. 8, 2017.
Japanese Office Action and English language translation from Appl. No. JP 2016-233881 dated Mar. 2, 2017.
Japanese Office Action, and English language translation, issued in Appl. No. JP 2016-233882 dated Sep. 25, 2017 (7 pages).
European Examination Report issued in Appl. No. EP 13 891 096.3 dated Feb. 21, 2018 (6 pp.).
Japanese Notice of Allowance issued in corresponding application, JP 2016-233882, dated Jun. 19, 2018, together with English translation (6 pages).
Michael Choti, "Abdominoperineal Resection with the LigaSure Vessel Sealing System and LigaSure Atlas 20 cm Open Instrument" Innovations That Work, .quadrature.Jun. 2003.
Chung et al., "Clinical Experience of Sutureless Closed Hemontoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyms PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al., "Comparison of Healing Process Following Ligation with Sutures and Bipolar Vessel Sealing" Surgical Technology International (2001).
US. Appl. No. 08/926,869, filed Sep. 10, 1997, James G. Chandler.
U.S Appl. No. 09/177,950, filed Oct. 23, 1998, Randel A. Frazier.
U.S Appl. No. 09/387,883, filed Sep. 1, 1999, Dale F. Schmaltz.
U.S Appl. No. 09/591,328, filed Jun. 9, 2000, Thomas P. Ryan.
U.S Appl. No. 12/336,970, filed Dec. 17, 2008, Paul R. Sremeich.
Japanese Office Action dated Sep. 2, 2016 in corresponding JP Application No. 2016-516040.
"Electrosurgery: A Historical Overview", Innovations in Electrosurgery; Sales/Product Literature; Dec. 31, 2000.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicoletomy Using the LigaSure Vessel Sealing System" Innovations That Work,. quadrature.Sep. 1999.
Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties at VHF Through Microwave Frequencies", IEEE Transactions on Microwave Theory and Techniques vol. MTT-28, No. 4, Apr. 1980 pp. 414-427.
Carus et al., "Initial Experience With the LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer"; Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for be Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/ Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Nashington University School of Medicine, St. Louis MO, Presented at AHPBA , Feb. 2001.
Seyfan et al. "Sutureless Closed Hemorrhoidectomy: A New Technique" Annals of Surgery vol. 234 No. 1 Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.

(56) References Cited

OTHER PUBLICATIONS

Craig Johnson. "Use of the LigaSure Vessel Sealing System in Bloodless Hemorrhoidectomy" That Work, Mar. 2000.
Levy et al. " Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Perl-Hilar Vessels in Laparoscopic Nephrectomy" Sales Product Literature.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Office Action issued in corresponding Korean Appl. No. 10-2016-7004068 dated Jan. 30, 2020, together with English Language translation (13 pages).
First Examination Report issued in corresponding Indian Appl. No. 201617001608 dated Sep. 17, 2020 (6 pages).
Office Action issued in corresponding Brazilian Appl. No. BR112016001520-7 dated Jul. 9, 2020 (4 pages) together with English language translation (3 pages).

* cited by examiner

METHOD OF ASSEMBLING AN ELECTROSURGICAL INSTRUMENT

CROSS-REFERENCE TO RELATED APPLICATIONS

The present application is a continuation application of U.S. patent application Ser. No. 14/906,072 filed on Jan. 19, 2016, which is a U.S. National Stage Application under 35 U.S.C. § 371(a) of PCT/CN2013/080947 filed on Aug. 7, 2013, the entire contents of each which are incorporated herein by reference.

BACKGROUND

1. Background of Related Art

The present disclosure relates to forceps used for open surgical procedures. More particularly, the present disclosure relates to a bipolar forceps for treating tissue that is capable of sealing and cutting tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation-"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

SUMMARY

The present disclosure relates to forceps used for open surgical procedures. More particularly, the present disclosure relates to a bipolar forceps for treating tissue that is capable of sealing and cutting tissue.

As is traditional, the term "distal" refers herein to an end of the apparatus that is farther from an operator, and the term "proximal" refers herein to the end of the electrosurgical forceps that is closer to the operator.

The bipolar forceps includes a mechanical forceps including first and second shafts. A jaw member extends from a distal end of each shaft. A handle is disposed at a proximal end of each shaft for effecting movement of the jaw members relative to one another about a pivot from a first position wherein the jaw members are disposed in spaced relation relative to one another to a second position wherein the jaw members cooperate to grasp tissue. A disposable housing is configured to releasably couple to one or both of the shafts. An electrode assembly is associated with the disposable housing and has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue. One or both of the electrodes includes a knife channel defined along its length. The knife channel is configured to receive a knife blade therethrough to cut tissue grasped between the jaw members. A switch is supported by the housing and is configured to initiate and terminate delivery of electrosurgical energy from the source of electrosurgical energy to the electrodes upon movement of the jaw members between the first and second positions. An actuation mechanism is at least partially disposed within the housing and configured to selectively advance the knife blade through the knife channel to cut tissue.

Additionally or alternatively, the bipolar forceps may also include a knife lockout mechanism configured to prohibit advancement of the knife blade into the knife channel when the jaw members are in the first position.

Additionally or alternatively, the knife lockout mechanism may move from a first position wherein the knife lockout mechanism engages the actuation mechanism when the jaw members are in the first position to a second position wherein the knife lockout mechanism disengages the actuation mechanism when the jaw members are in the second position to permit selective advancement of the knife blade through the knife channel.

Additionally or alternatively, at least one of the shafts may be configured to engage the knife lockout mechanism upon movement of the jaw members to the second position and move the knife lockout mechanism out of engagement with the actuation mechanism to permit advancement of the knife blade through the knife channel.

Additionally or alternatively, the switch may be mechanically coupled to a depressible button extending from the housing and configured to be engaged by one of the shafts upon movement of the jaw members to the second position.

Additionally or alternatively, the pivot may define a longitudinal slot therethrough and the knife blade may be configured to move within the longitudinal slot upon translation thereof.

Additionally or alternatively, the bipolar forceps may also include at least one handle member extending from the housing. The at least one handle member may be operably coupled to the actuation mechanism and configured to effect advancement of the knife blade through the knife channel.

Additionally or alternatively, each of the electrodes may include an electrically conductive sealing surface and an insulating substrate coupled thereto.

Additionally or alternatively, each of the electrodes may include at least one mechanical interface configured to complement a corresponding mechanical interface on one of the jaw members to releasably couple the electrode to the jaw member.

Additionally or alternatively, the actuation mechanism may include a biasing member configured to bias the actuation mechanism to an unactuated position.

Additionally or alternatively, the bipolar forceps may also include a knife guide supported in the housing and having a longitudinal slot defined therethrough that receives the knife blade therein to align the knife blade with the knife channel.

According to another aspect of the present disclosure, a bipolar forceps is provided. The bipolar forceps includes a mechanical forceps including first and second shafts each having a jaw member extending from its distal end. A handle is disposed at a proximal end of each shaft for effecting movement of the jaw members relative to one another about a pivot from a first position wherein the jaw members are disposed in spaced relation relative to one another to a second position wherein the jaw members cooperate to grasp tissue. A disposable housing has opposing halves configured to releasably couple to each other to at least partially encompass one or both of the shafts. An electrode assembly is associated with the disposable housing and has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue held therebetween to effect a tissue seal. At least one of the electrodes includes a knife channel defined along a length thereof, the knife channel configured to receive a knife blade therethrough to cut tissue grasped between the jaw members. An actuation mechanism is at least partially disposed within the housing and is configured to selectively advance the knife blade through the knife channel to cut tissue. A depressible activation button extends from a proximal portion of the housing and is operably coupled to a switch supported by the proximal portion of the housing. The activation button is configured to depress upon approximation of the shaft members such that the switch initiates delivery of electrosurgical energy from the source of electrosurgical energy to the electrode assembly. A knife lockout mechanism is configured to move from a first position wherein the knife lockout mechanism engages the actuation mechanism to prohibit advancement of the knife blade through the knife channel when the jaw members are in the first position to a second position wherein the knife lockout mechanism disengages the actuation mechanism when the jaw members are in the second position to permit advancement of the knife blade through the knife channel.

Additionally or alternatively, at least one of the shafts may be configured to engage the knife lockout mechanism upon movement of the jaw members to the second position and move the knife lockout mechanism out of engagement with the actuation mechanism and permit advancement of the knife blade through the knife channel.

Additionally or alternatively, the pivot may define a longitudinal slot therethrough and the knife blade may be configured to advance through the longitudinal slot upon translation thereof.

Additionally or alternatively, the bipolar forceps may also include a knife guide supported in the housing and having a longitudinal slot defined therethrough that receives the knife blade therein to align the knife blade with the knife channel.

Additionally or alternatively, the bipolar forceps may also include at least one handle member operably coupled to the actuation mechanism and moveable from an unactuated configuration to an actuated configuration to effect advancement of the knife blade through the knife channel.

Additionally or alternatively, the bipolar forceps may also include a knife kickback configured to force the at least one handle member from the actuated configuration to the unactuated configuration upon movement of the jaw members from the second position to the first position.

According to another aspect of the present disclosure, a bipolar forceps is provided. The bipolar forceps includes a mechanical forceps including first and second shafts each having a jaw member extending from its distal end. A handle is disposed at a proximal end of each shaft for effecting movement of the jaw members relative to one another about a pivot from a first position wherein the jaw members are disposed in spaced relation relative to one another to a second position wherein the jaw members cooperate to grasp tissue therebetween. A disposable housing is configured to be releasably coupled to at least one of the shafts. An electrode assembly is configured to releasably couple to the jaw members and is adapted to connect to a source of electrosurgical energy to allow selective conduction of electrosurgical energy through tissue held between the jaw members to effect a tissue seal. At least one of the jaw members includes a knife channel defined along its length. The knife channel is configured to receive a knife blade therethrough to cut tissue grasped between the jaw members. A knife guide is supported in the housing and has a longitudinal slot defined therethrough that receives the knife blade therein to align the knife blade with the knife channel. An actuation mechanism is at least partially disposed within the housing and is configured to selectively advance the knife blade through the knife channel to cut tissue. A switch is supported by the housing and is configured to initiate and terminate delivery of electrosurgical energy from the source of electrosurgical energy to the electrode assembly upon movement of the jaw members between the first and second positions. At least one handle member extends from the housing. The at least one handle member is operably coupled to the actuation mechanism and is configured to effect advancement of the knife blade through the knife channel. A knife lockout mechanism is configured to be engaged by at least one of the shaft members and move the knife lockout mechanism from a first position wherein the knife lockout mechanism engages the actuation mechanism to prohibit advancement of the knife blade into the knife channel when the jaw members are in the first position to a second position wherein the knife lockout mechanism disengages the actuation mechanism when the jaw members are in the second position to permit selective advancement of the knife blade through the knife channel.

Additionally or alternatively, the knife guide may extend through a longitudinal slot defined through the pivot.

Additionally or alternatively, the bipolar forceps may also include a knife kickback configured to force the at least one handle member from the actuated configuration to the unactuated configuration upon movement of the jaw members from the second position to the first position.

According to another aspect of the present disclosure, a method of assembling a bipolar forceps is provided. The method includes providing a first assembly including first and second shafts operably coupled to each other about a pivot. Each of the first and second shafts has a jaw member extending from its distal end. The first and second shafts are moveable relative to each other about the pivot to grasp tissue between the jaw members. The method also includes providing a second assembly including a knife blade operably coupled to a knife actuation mechanism configured to move the knife blade longitudinally through a passageway defined through the pivot of the first assembly to cut tissue grasped between the jaw members. The method also includes providing a housing configured to releasably couple to at least one of the shafts to at least partially house the knife blade and the knife actuation mechanism. The method also includes placing the second assembly relative to the first assembly and releasably coupling the housing to at least one of the shafts to operably couple the second assembly to the first assembly.

Additionally or alternatively, placing the second assembly relative to the first assembly may also include inserting the knife blade at least partially through the passageway.

Additionally or alternatively, placing the second assembly relative to the first assembly may include placing the knife actuation mechanism relative to at least one of the shaft members.

Additionally or alternatively, the first assembly may be a reusable mechanical forceps.

Additionally or alternatively, the second assembly may be removable from the first assembly.

Additionally or alternatively, the method may also include coupling an electrode assembly to the jaw members, the electrode assembly configured to connect to a source of electrosurgical energy.

According to another aspect of the present disclosure, a bipolar forceps is provided. The bipolar forceps includes a mechanical forceps including first and second shafts. Each of the shafts has a jaw member extending from its distal end. The shafts are moveable relative to one another about a pivot from a first position wherein the jaw members are disposed in spaced relation relative to one another to a second position wherein the jaw members cooperate to grasp tissue therebetween. Each of the shafts has an interior side facing the other shaft and an exterior side opposite the interior side. The bipolar forceps also includes a knife assembly including a knife blade operably coupled to a knife actuation mechanism configured to actuate the knife blade longitudinally through a passageway defined through the pivot to cut tissue grasped between the jaw members. The knife assembly is operably coupleable to the mechanical forceps from the exterior side of one of the shafts such that the knife blade is at least partially insertable through the passageway from the exterior side of one of the shafts and the knife actuation mechanism is releasably coupleable to the mechanical forceps from the exterior side of one of the shafts. The bipolar forceps also includes a housing configured to releasably couple to at least one of the shafts to operably couple the knife assembly to the mechanical forceps. The bipolar forceps also includes an electrode assembly having a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue held between the electrodes.

Additionally or alternatively, the knife actuation mechanism may be releasably coupleable to the mechanical forceps by moving the knife actuation mechanism relative to one of the shafts from an exterior side thereof while inserting the knife blade at least partially through the passageway from the exterior side of the same shaft.

Additionally or alternatively, at least one of the electrodes may include a knife channel defined along its length. The knife channel may be configured to receive the knife blade therethrough to cut tissue grasped between the jaw members.

Additionally or alternatively, the shafts may be disposed relative to the passageway such that the knife blade is insertable through the passageway from the exterior of one of the shafts.

BRIEF DESCRIPTION OF THE DRAWINGS

Various embodiments of the subject instrument are described herein with reference to the drawings wherein.

DETAILED DESCRIPTION

Figure 1:
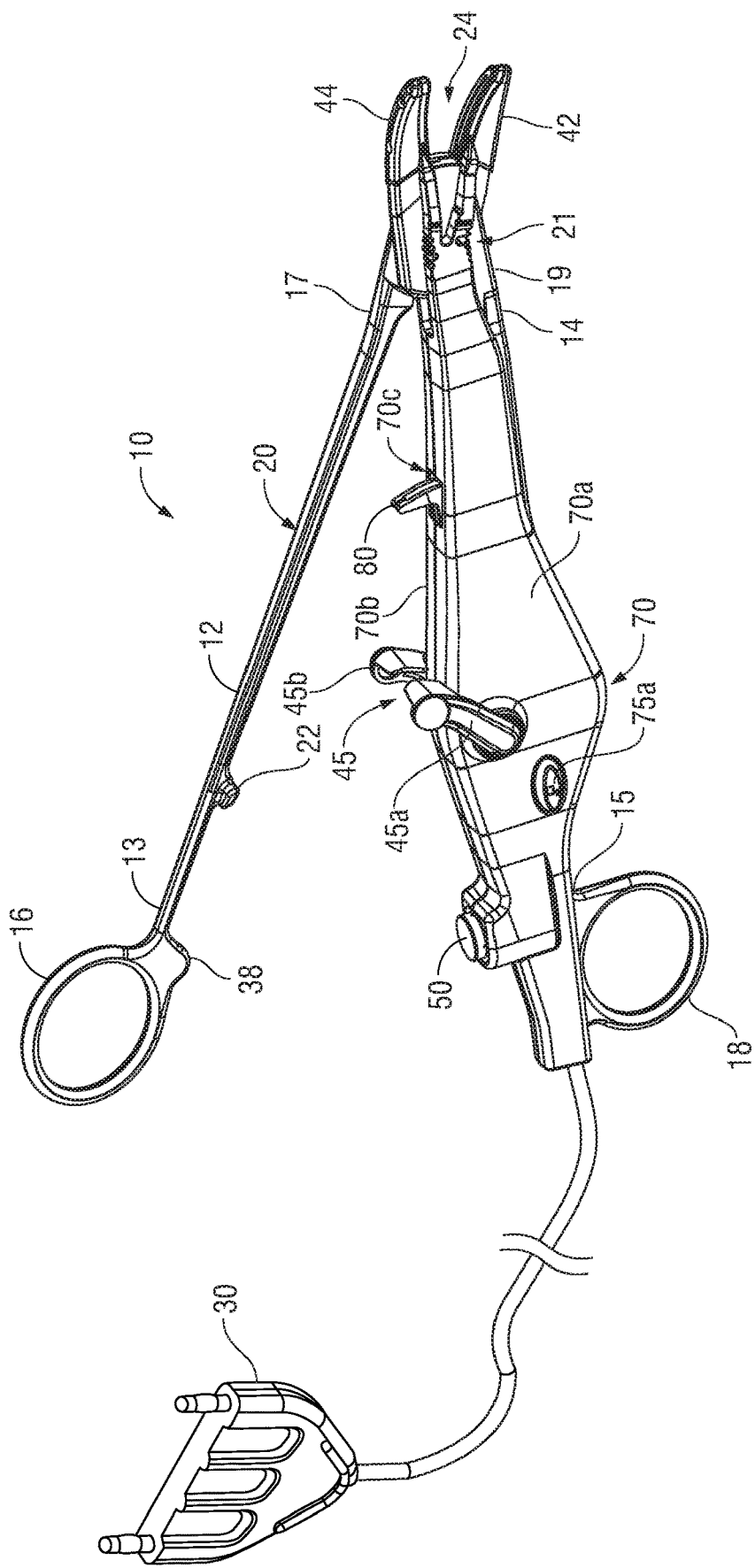
FIG. 1 is a perspective view of a bipolar forceps according to an embodiment of the present disclosure including a mechanical forceps, a disposable housing, and a disposable electrode assembly.
Figure 2:
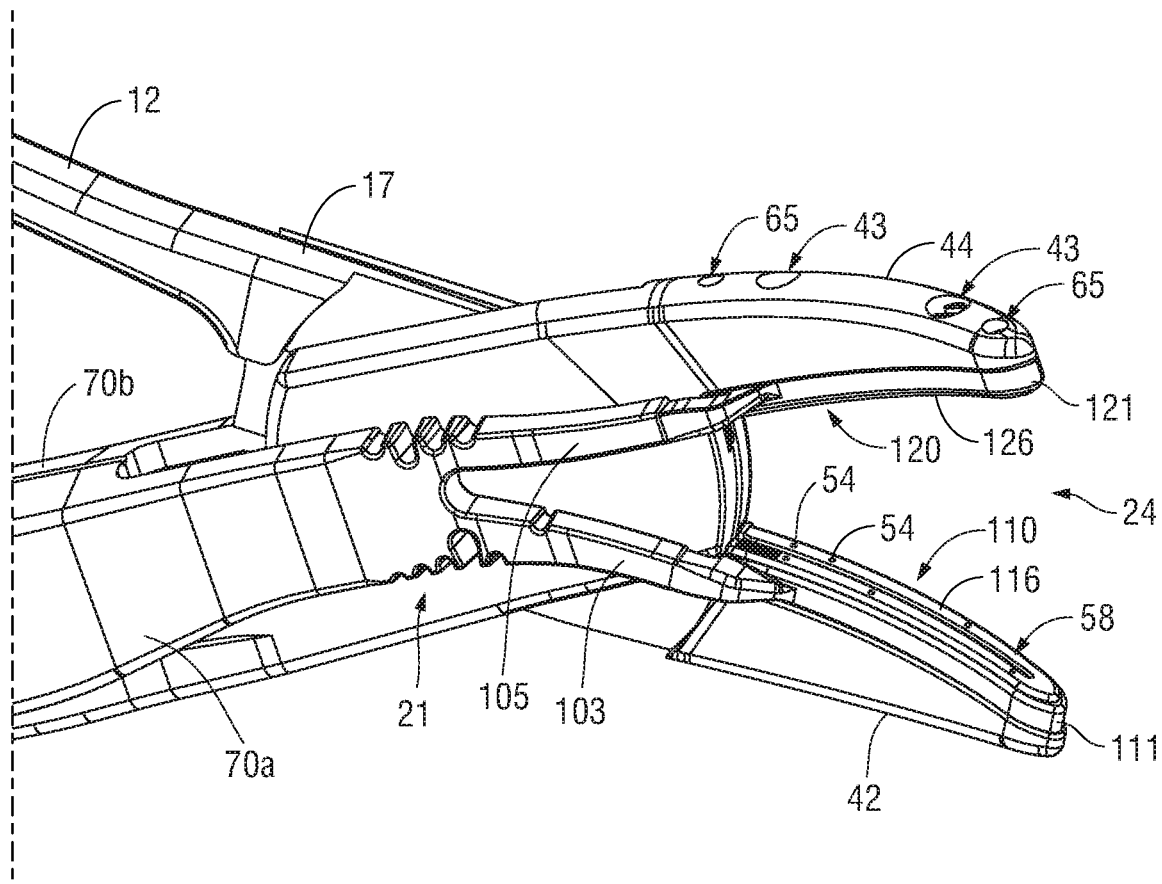
FIG. 2 is an enlarged, perspective view of a distal end of the bipolar forceps of FIG. 1.
Figure 3:
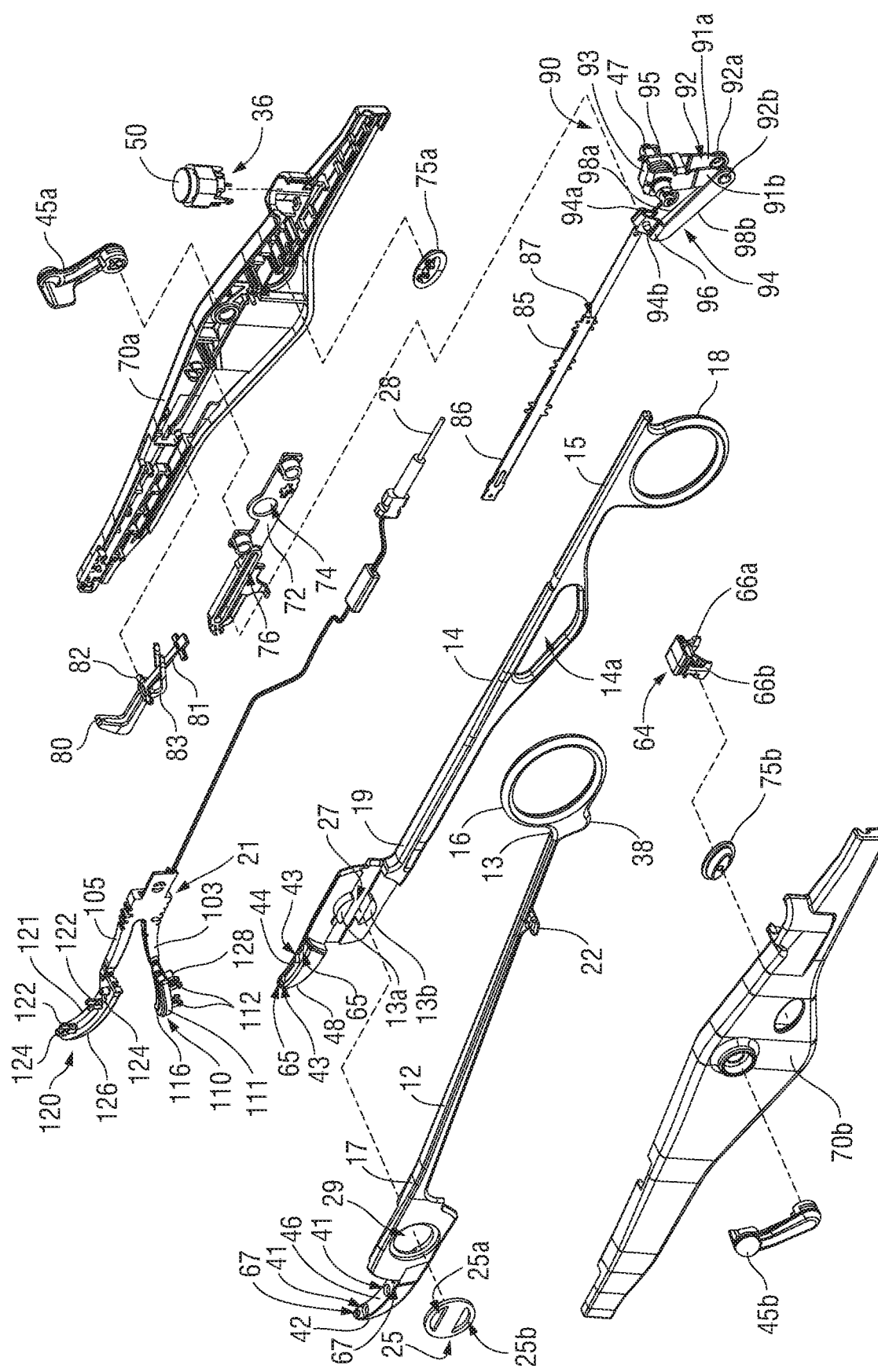
FIG. 3 is a perspective view of the bipolar forceps of FIG. 1 with parts separated.

Referring initially to FIGS. 1-3, a bipolar forceps 10 for use with open surgical procedures includes a mechanical forceps 20 having an end effector 24 and a disposable electrode assembly 21. Mechanical forceps 20 includes first and second elongated shaft members 12 and 14. Elongated shaft member 12 includes proximal and distal end portions 13 and 17, respectively, and elongated shaft member 14 includes proximal and distal end portions 15 and 19, respectively. Disposed at proximal end portions 13, 15 of shaft members 12, 14 are handle members 16 and 18, respectively, that are configured to allow a user to effect movement of at least one of the shaft members 12 and 14 relative to the other. The end effector 24 includes opposing jaw members 42, 44 that extend from the distal end portions 17 and 19 of shaft members 12 and 14, respectively. The jaw members 42, 44 are movable relative to each other in response to movement of shaft members 12, 14. At least one of the shaft members, e.g., shaft member 12, includes a tang 99 that facilitates manipulation of forceps 20 during use.

Figure 8:
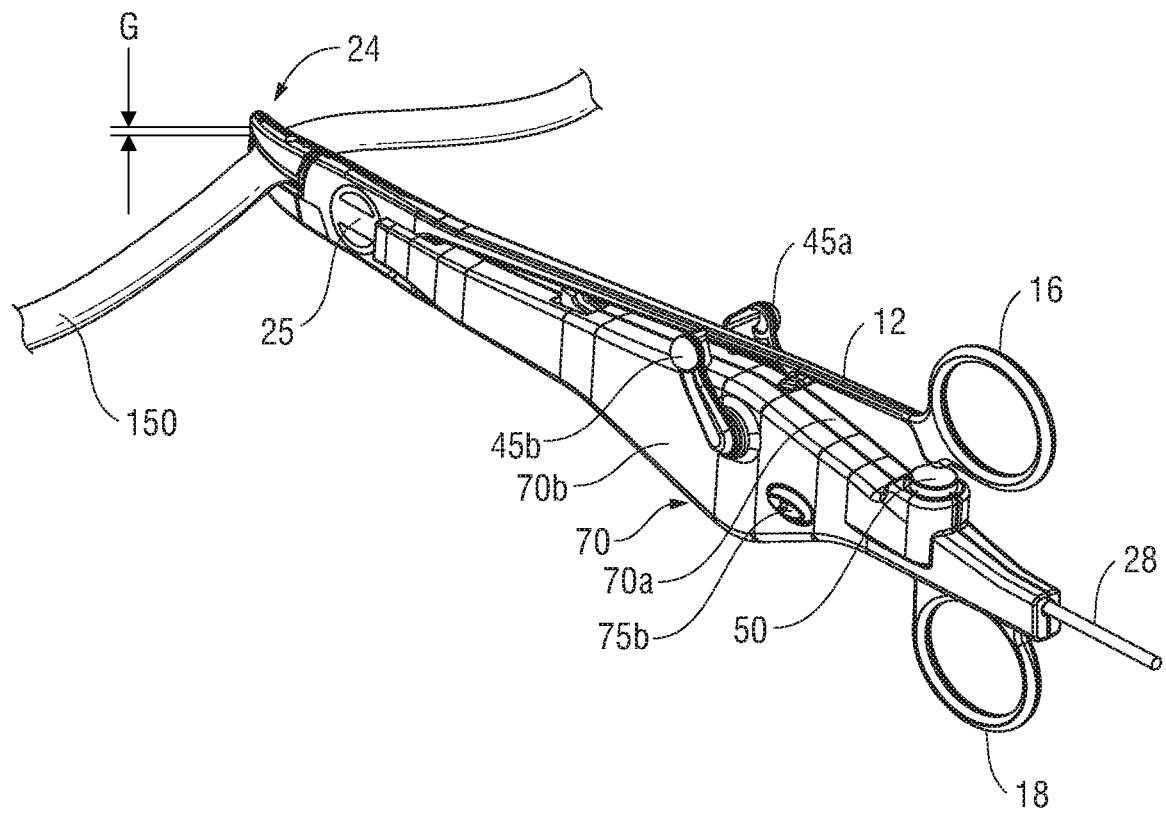
FIG. 8 is a perspective view of the bipolar forceps of FIG. 1 grasping tissue to effect a tissue seal.

Shaft members 12 and 14 are affixed to one another about a pivot 25 (FIG. 3) such that movement of shaft members 12, 14, imparts movement of the jaw members 42, 44 from an open configuration (FIG. 9A) wherein the jaw members 44, 42 are disposed in spaced relation relative to one another to a clamping or closed configuration (FIGS. 9B and 9C) wherein the jaw members 42, 44 cooperate to grasp tissue 150 therebetween (FIG. 8). In some embodiments, the forceps 10 may be configured such that movement of one or both of the shaft members 12, 14 causes only one of the jaw members to move with respect to the other jaw member. Pivot 25 includes a pair of generally semi-circular shaped apertures 25a, 25b disposed therethrough and is configured to be seated in a pivot aperture 29 (FIG. 3) such that pivot 25 is permitted to freely rotate within pivot aperture 29, as further detailed below.

Referring to FIGS. 2 and 3, disposable electrode assembly 21 is configured to releasably couple to mechanical forceps 20, as detailed below, and is operably coupled to a housing 70 having a pair of housing halves 70a, 70b configured to matingly engage and releasably encompass at least a portion of shaft member 14. Housing 70 also serves to at least partially house a knife 85 having a sharpened distal cutting edge 89 (FIG. 9D), a knife guide 86 having a longitudinal slot 87 (FIG. 3) configured to receive the knife blade 85 therein, and a knife actuation mechanism 90 configured to effect advancement of the knife blade 85 through a knife channel 58 (FIG. 2) defined in one or both electrodes 110, 120 to transect tissue, as further detailed below. An interior of each of housing halves 70a, 70b may include a plurality of cooperating mechanical interfaces disposed at various locations to effect mechanical coupling of housing halves 70a, 70b to form housing 70. A pair of opposing push buttons 75a, 75b are disposed on housing halves 70a, 70b, respectively, and are accessible from an exterior of housing 70 such that a user may press buttons 75a, 75b inwardly relative to the housing 70 to release the mechanical coupling of housing 70 and shaft member 14. A resilient member 64 (FIG. 3) is operably coupled to an interior of housing 70 and releasably coupled to shaft member 14. Resilient member 64 includes a pair of resilient extensions 66a, 66b that are operably coupled to buttons 75a, 75b, respectively. Pressing buttons 75a, 75b inwardly relative to housing 70 imparts a biasing force on resilient extensions 66a, 66b such that resilient extensions 66a, 66b flex inward toward each other, which in turn causes resilient member 64 to release from shaft member 14. Once resilient member 64 is released from shaft member 14, housing 70 may be uncoupled from mechanical forceps 20. Thus, the user is provided with the ability to uncouple housing 70 from mechanical forceps 20 simply by pressing buttons 75a, 75b inwardly relative to housing 70.

The placement of buttons 75a, 75b relative to housing 70 illustrated in the drawings should not be construed as limiting, as buttons 75a, 75b may be disposed on any suitable location of housing 70. For example, buttons 75a, 75b may be disposed on a proximal end of housing 70 adjacent handle member 18 and proximal to a depressible activation button 50 (FIG. 1) described in detail below. In some embodiments, buttons 75a, 75b and/or resilient member 64 may include wire-routing features formed therein for routing wires through housing 70.

Figure 4:
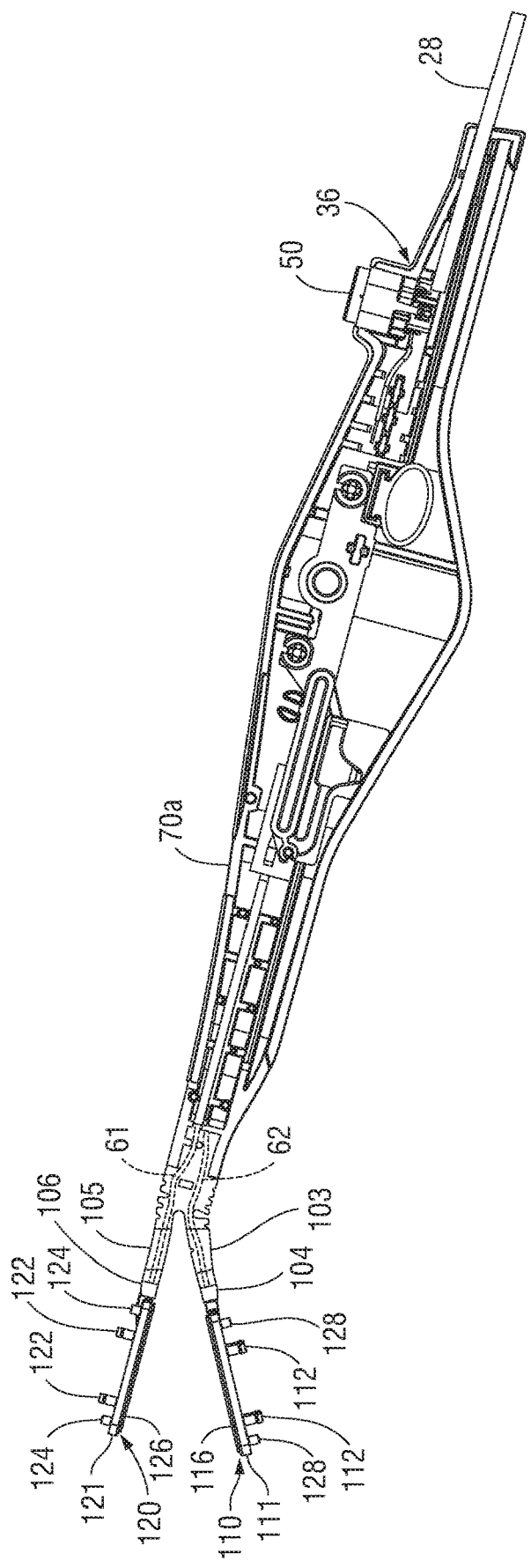
FIG. 4 is an enlarged, internal side view of the disposable housing and the disposable electrode assembly of FIG. 1 with parts partially removed.
Figure 6:
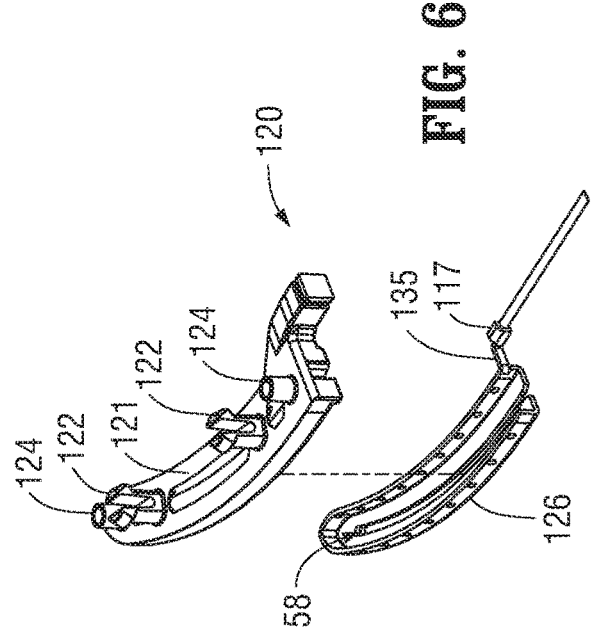
FIGS. 6 and 7 are greatly-enlarged perspective views of electrodes of the disposable electrode assembly of FIG. 1 with parts separated.
Figure 5:
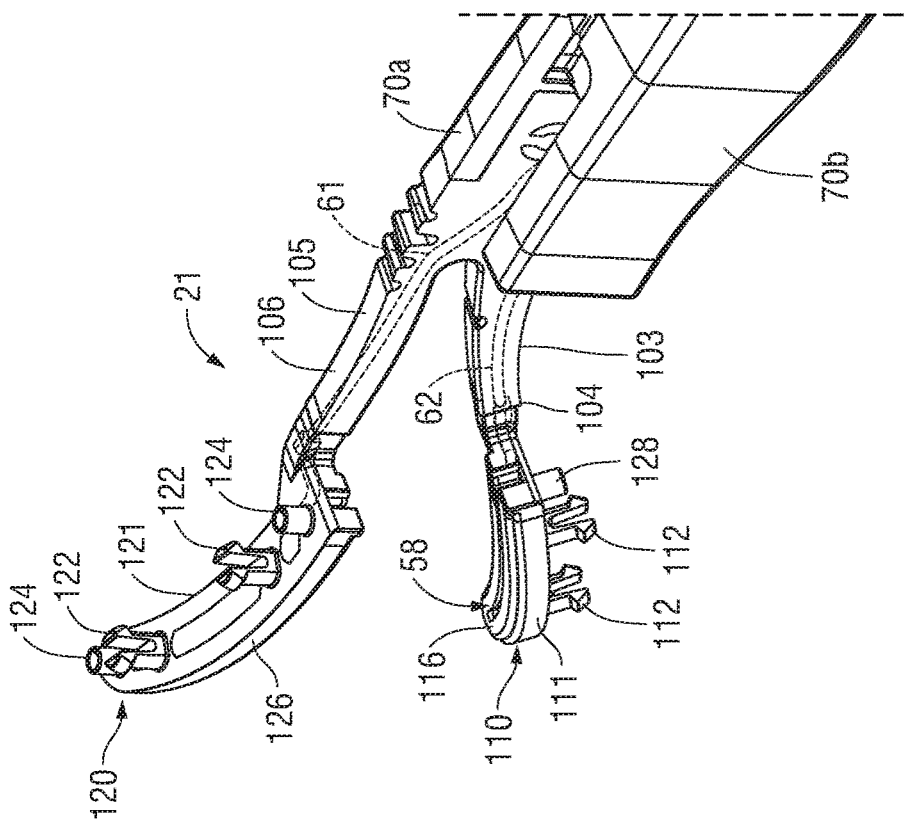
FIG. 5 is a greatly-enlarged, perspective view of the disposable electrode assembly of FIG. 1.

As shown in FIGS. 4 and 5, a pair of wires 61 and 62 are electrically connected to the electrodes 120 and 110, respectively, and are bundled to form a cable 28 that extends through housing 70 and terminates at a terminal connector 30 (FIG. 1) configured to mechanically and electrically couple to a suitable energy source, such as an electrosurgical generator (not shown). Examples of electrosurgical generators are the LIGASURE® Vessel Sealing Generator and the ForceTriad® Generator sold by Covidien. In some embodiments, a suitable energy source may be a battery (not shown) supported by the housing 70 and electrically connected to the electrodes 110, 120.

Referring now to FIGS. 3-7, electrode assembly 21 is bifurcated such that two prong-like members 103 and 105 extend distally therefrom to support electrodes 110 and 120, respectively. Electrode 120 includes an electrically conductive sealing surface 126 configured to conduct electrosurgical energy therethrough and an electrically insulative substrate 121 that serves to electrically insulate sealing surface 126 from jaw member 44. Sealing surface 126 and substrate 121 are attached to one another by any suitable method of assembly such as, for example, snap-fit engagement or by overmolding substrate 121 to sealing surface 126. In some embodiments, substrate 121 is made from an injection molded plastic material. Substrate 121 includes a plurality of bifurcated anchor members 122 extending therefrom that are configured to compress inwardly during insertion into a corresponding plurality of sockets 43 disposed at least partially through an inner facing surface 48 (FIG. 3) of jaw member 44 and subsequently expand to releasably engage corresponding sockets 43 after insertion to couple electrode 120 to inner facing surface 48. Substrate 121 also includes one or more alignment pins 124 (FIG. 4) that are configured to engage a corresponding aperture 65 disposed at least partially through inner facing surface 48 of jaw member 44 to ensure proper alignment of electrode 120 with jaw member 44 during assembly. Conductive sealing surface 126 includes an extension 135 having a wire crimp 117 (FIG. 6) configured to be inserted into the distal end 106 of prong 105 of electrode assembly 21 and electrically connect to wire 61 disposed therein (FIG. 5).

Figure 7:
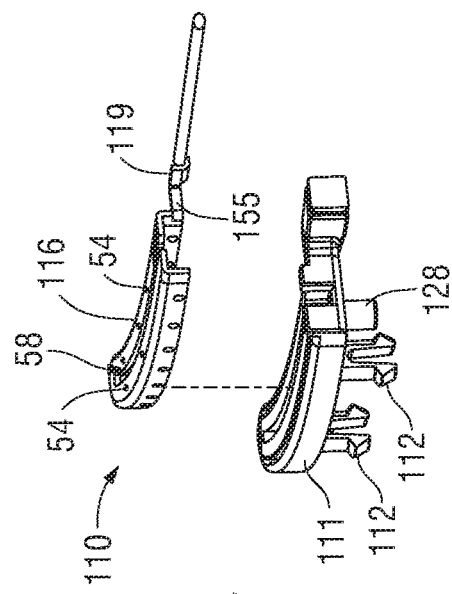

Substantially as described above with respect to electrode 120, electrode 110 includes an electrically conductive sealing surface 116 configured to conduct electrosurgical energy therethrough and an electrically insulative substrate 111 attached thereto, as shown in FIG. 7. Substrate 111 includes a plurality of bifurcated anchor members 112 extending therefrom that are configured to compress inwardly during insertion into a corresponding plurality of sockets 41 disposed at least partially through an inner facing surface 46 (FIG. 3) of jaw member 42 and subsequently expand to releasably engage corresponding sockets 41 after insertion to couple electrode 110 to inner facing surface 46. Substrate 111 also includes one ore more alignment pins 128 (FIG. 4) that are configured to engage a corresponding aperture 67 disposed at least partially through inner facing surface 46 of jaw member 42 to ensure proper alignment of electrode 110 with jaw member 42 during assembly. Sealing surface 116 includes an extension 155 having a wire crimp 119 (FIG. 7) extending therefrom configured to be inserted into the distal end 104 of prong 103 of electrode assembly 21 and electrically connect to wire 62 disposed therein (FIG. 5).

Referring to FIG. 4, at least one of the prong members 103, 105 is flexible such that prong members 105 and 103 are readily moveable relative to each other. In some embodiments, the electrode assembly 21 is removably attached to the mechanical forceps 20 by initially moving prongs 103, 105 towards each other. While jaw members 42, 44 are in an open configuration, the electrodes 120 and 110 may be slid between opposing jaw members 44 and 42 such that anchor members 122 and 112 and guide pins 124 and 128, respectively, may be aligned with and releasably inserted into corresponding sockets 43 and 41 or apertures 65 and 67, respectively, to couple electrodes 120 and 110 with jaw member 44 and 42, respectively. Housing halves 70a, 70b may then be coupled to form housing 70 to encompass at least a portion of shaft member 14 in the manner described above.

Figure 9A:
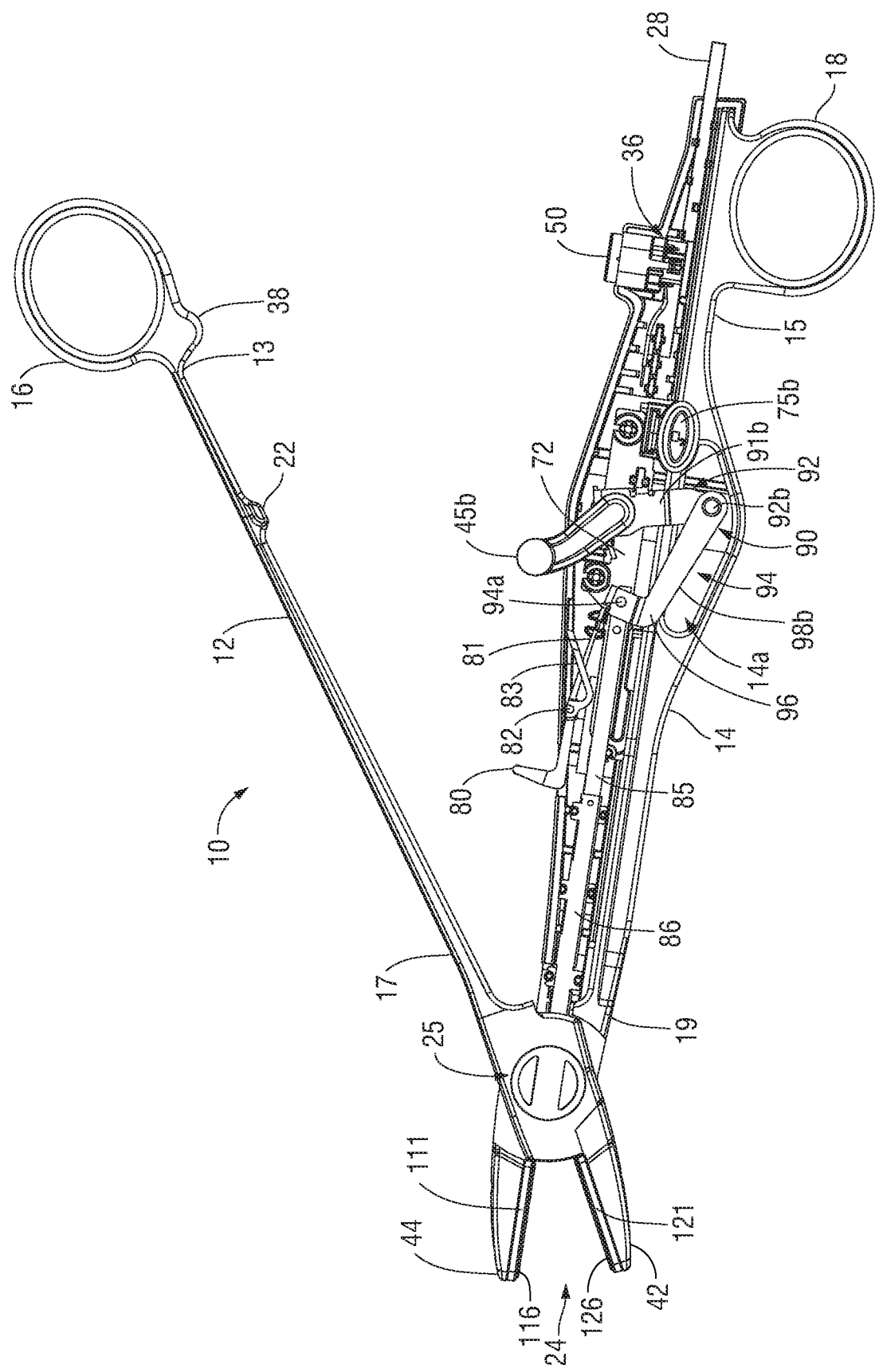
FIGS. 9A-9D are generally internal, side views of the bipolar forceps of FIG. 1 depicting a sequence of motions to illustrate operation of the bipolar forceps.
Figure 9B:
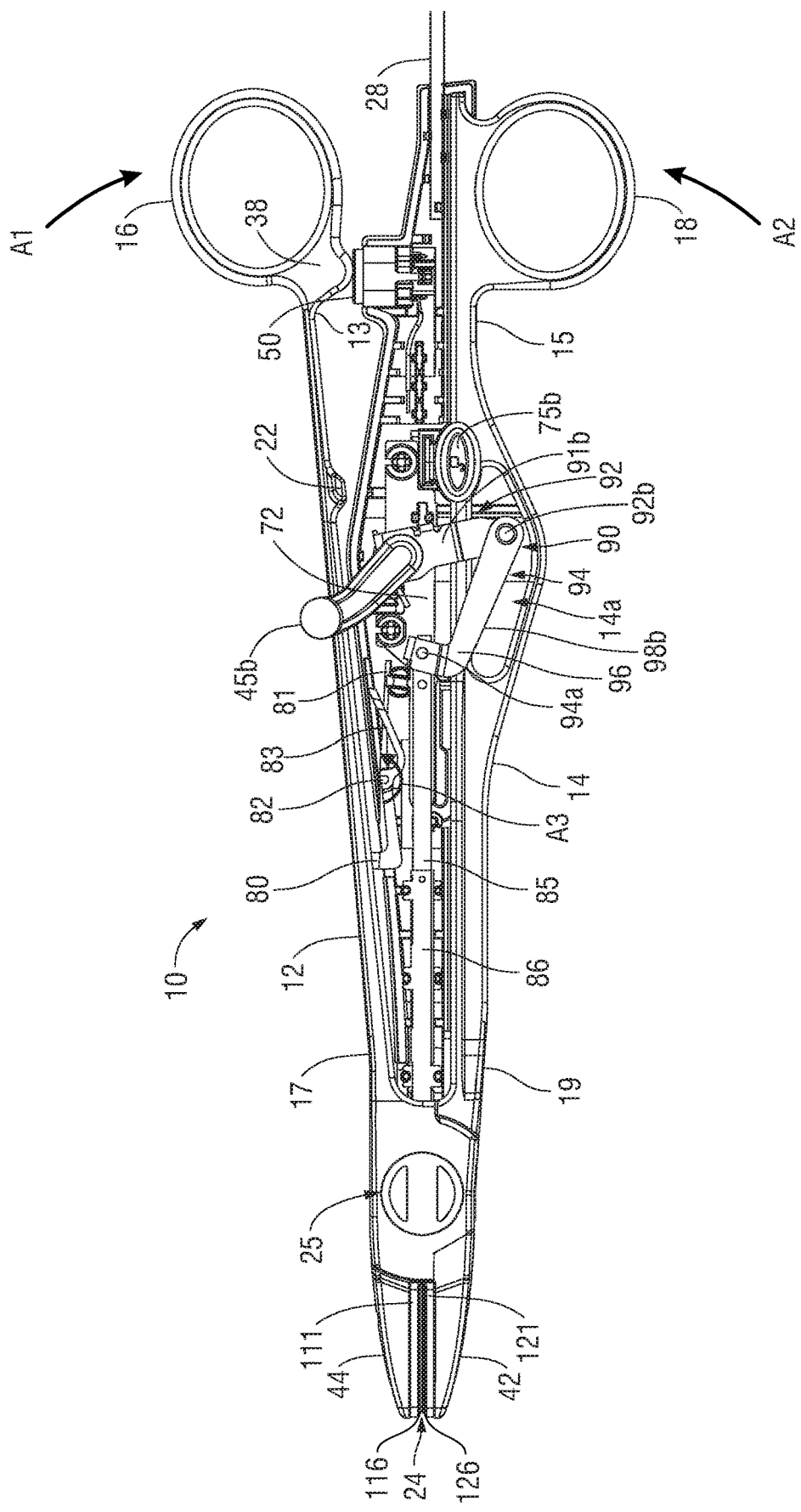

To electrically control the end effector 24, a depressible activation button 50 (FIG. 1) extends from a proximal portion of housing 70 and is operable by a user to initiate and terminate the delivery of electrosurgical energy to end effector 24. Mechanically coupled to depressible activation button 50 is a switch 36 (FIG. 4) supported within housing 70 and electrically interconnected between wires 61, 62 and a suitable energy source, such as an electrosurgical generator (not shown). Depressible activation button 50 is engageable by a button activation post 38 extending from proximal end 13 of shaft member 12 upon movement of shaft members 12, 14 to an actuated or approximated position (FIG. 9B). During use, for example, engagement of depressible activation button 50 with button activation post 38 serves to activate switch 36 to initiate delivery of electrosurgical energy to end effector 24 for effecting a tissue seal, and disengagement of button activation post 38 from depressible activation button 50 serves to deactivate switch 36 to terminate delivery of electrosurgical energy to end effector 24. In some embodiments, delivery of electrosurgical energy to end effector 24 may also be terminated by the electrosurgical generator based on any suitable parameters, e.g., sensed tissue properties, time parameters, sensed energy properties, etc.

Once a tissue seal is established, the knife blade 85 may be advanced through the knife channel 58 to transect the sealed tissue, as detailed below. However, in some embodiments, knife blade 85 may be advanced through the knife channel 58 before, during, or after tissue sealing. In some embodiments, a knife lockout mechanism is provided to prevent extension of the knife blade 85 into the knife channel 58 when the jaw members 42, 44 are in the open configuration, thus preventing accidental or premature transection of tissue, as described below.

With reference to FIG. 3, the knife actuation mechanism 90 is operably associated with a trigger 45 (FIG. 1) having opposing handle members 45a, 45b extending from opposing sides of housing 70. The housing 70 is shaped to complement an outwardly extending cutout portion 14a of shaft member such that upon coupling of housing halves 70a, 70b about shaft member 14, the knife actuation mechanism 90 is encompassed by the housing 70 (FIG. 1). Upon actuation of handle members 45a, 45b, the knife actuation mechanism 90 responds utilizing a series of inter-cooperating elements to actuate the knife blade 85 through the knife channel 58 to sever tissue grasped between jaw members 42, 44, as detailed below with reference to FIG. 9C. The knife actuation mechanism 90 includes a first link 92 having an arcuate portion 93 bridging opposing linear extensions 91a, 91b and a second link 94 having an arcuate portion 96 bridging opposing linear extensions 98a, 98b. Arcuate portion 93 is operably coupled to a shaft member 47 and linear extensions 91a, 91b are operably coupled to linear extensions 98a, 98b of second link 94 by opposing pivot pins 92a, 92b, respectively. Shaft member 47 extends laterally through housing 70 to operably connect handle members 45a, 45b from opposing sides of housing 70. Arcuate portion 96 of second link 94 is operably coupled to a proximal end of the knife blade 85 by a pivot pin 94a extending through arcuate portion 96. As can be seen in FIG. 3, each of first and second links 92, 94 are generally u-shaped components so that opposing linear extensions 91a, 91b and 98a, 98b define a space therebetween through which shaft member 14 may pass unimpeded during assembly and during actuation of knife actuation mechanism 90. This generally u-shaped configuration allows first and second links 92, 94 to extend around shaft member 14.

A mechanical interface 72 is supported within housing 70 and is disposed between knife actuation mechanism 90 and one of the housing halves (e.g., housing half 70a). Mechanical interface 72 includes a through hole 74 through which shaft member 47 extends and a longitudinal channel 76 through which at least a portion of pivot pin 94a translates during actuation of knife blade 85. More specifically, pivot pin 94a extends outwardly from opposing sides of arcuate portion 96, as shown in FIG. 3. At least a portion of pivot pin 94a that extends outwardly from one opposing side of arcuate portion 96 is received within longitudinal channel 76. As handle members 45a, 45b are moved from an unactuated configuration (FIGS. 9A and 9B) to an actuated configuration (FIG. 9C) to advance the knife blade 85 distally through knife channel 58, pivot pin 94a translates distally through longitudinal channel 76 from a proximal portion thereof to a distal portion thereof. In this way, longitudinal channel 76 serves to constrain upward and downward movement of pivot pin 94a, thereby ensuring linear longitudinal motion of knife blade 85. Mechanical interface 72 may also serve as a protective cover for wires 61, 62 as wires pass through housing half 70a, for example, by separating wires 61, 62 from knife actuation mechanism 90 such that wires 61, 62 do not interfere with knife actuation mechanism 90 during actuation thereof. Mechanical interface 72 also serves to prevent inadvertent actuation of knife actuation mechanism 90 prior to coupling of mechanical forceps 20 to the remaining components of forceps 10, as described in further detail below.

A biasing member 95 (e.g., a torsion spring) is disposed coaxially about at least a portion of the shaft member 47 (FIG. 3) between the first link 92 and handle member 45a. The biasing member 95 is operably coupled at one end to a portion of the first link 92 and at the other end to a suitable mechanical interface within the housing 70 that stabilizes biasing member 95 during use of the knife actuation mechanism 90. The biasing member 95 serves to bias the trigger 45 such that subsequent to actuation of the knife blade 85 through the knife channel 58 (FIG. 9C), handle members 45a, 45b are biased to return to an unactuated position (FIGS. 9A and 9B), thereby retracting the knife blade 85 proximally to an unactuated position (FIGS. 9A and 9B). A knife kickback 22 is disposed along a portion of shaft member 12 and, upon movement of shaft members 12, 14 from the closed configuration (FIG. 9B) to the open configuration (FIG. 9A), knife kickback 22 is configured to engage handle members 45a, 45b (FIG. 9D) in the event that handle members 45a, 45b do not return to an unactuated position (FIGS. 9A and 9B) following actuation of the knife actuation mechanism 90, as detailed below with reference to FIG. 9D.

With reference to FIG. 3, pivot 25 includes a pair of apertures 25a, 25b disposed therethrough that are configured to receive a pair of complementary raised portions 13a, 13b therein, respectively, extending from the distal end portion 19 of shaft member 14 and defining a longitudinal passageway 27 therebetween. Raised portions 13a, 13b extend sufficiently from the distal portion of shaft member 14 so that apertures 25a, 25b may receive raised portions 13a, 13b therein, respectively, while maintaining pivot 25 in spaced relation with the distal portion of shaft member 14 to allow the knife guide 86 to be received through passageway 27. Movement of shaft members 12, 14 relative to each other causes rotational movement of pivot 25 within pivot aperture 29.

Knife guide 86 is supported within the housing 70 between the end effector 24 and the knife actuation mechanism 90 and extends through passageway 27. Knife guide 86 includes suitable mechanical features (e.g., protrusions) that interface with corresponding suitable mechanical features disposed on shaft member 14 to provide upward and downward location control of knife guide 86. The longitudinal slot 87 defined through knife guide 86 (FIG. 3) provides lateral support to the knife blade 85 and constrains side-to-side lateral motion of the knife blade 85. Thus, the knife guide 86 serves to urge the knife blade 85 into a central position relative to end effector 24, thereby ensuring proper alignment of the knife blade 85 as the knife blade 85 enters the knife channel 58 (FIG. 2) defined in electrodes 110, 120.

In some embodiments, the forceps 10 includes a knife blade lockout mechanism that serves to prevent advancement of the knife blade 85 into the knife channel 85 when the jaw members 42, 44 are in the open configuration (FIG. 9A). With reference to FIG. 3, one embodiment of a knife blade lockout mechanism is shown. The knife blade lockout mechanism is pivotally supported within housing 70 (FIGS. 9A-9D) and includes a flexible safety link 81 operably coupled about a pivot pin 82 with a biasing member 83 and an engagement member 80. In the open configuration of jaw members 42, 44, the knife blade 85 is in an unactuated position (FIGS. 9A and 9B) and the safety link 81 is engaged with the arcuate portion 96 of the second link 94 (FIG. 9A) such that distal advancement of knife blade 85 is prohibited. As shown in FIG. 3, safety link 81 is depicted having a t-shaped configuration. However, this t-shaped configuration should not be construed as limiting, in that safety link 81 may be any shape or configuration suitable to engage and disengage arcuate portion 96. In the illustrated embodiment, the t-shaped configuration of safety link 81 provides load transfer to housing 70 upon actuation of knife actuation mechanism 90, thereby preventing damage to safety link 81 due to an overload condition.

To prevent inadvertent actuation of knife blade 85 prior to coupling of mechanical forceps 20 to the remaining components of forceps 10 (e.g., housing 70, mechanical interface 72, knife actuation mechanism 90, knife blade 85, knife guide 86, knife blade lockout mechanism, etc.), a portion of mechanical interface 72 is engaged with and in the distal path of the arcuate portion 96 of the second link 94 such that distal advancement of knife blade 85 is prohibited. Upon coupling of mechanical forceps 20 to the remaining component of forceps 10, shaft member 14 deflects mechanical interface 72 to remove the previously engaged portion of mechanical interface 72 from the distal path of the arcuate portion 96. Thus, mechanical interface 72 prevents inadvertent actuation of knife blade 85 prior to assembly of forceps 10, and the knife blade lockout mechanism prevents inadvertent actuation of knife blade 85 once forceps 10 is assembled.

Figure 9C:
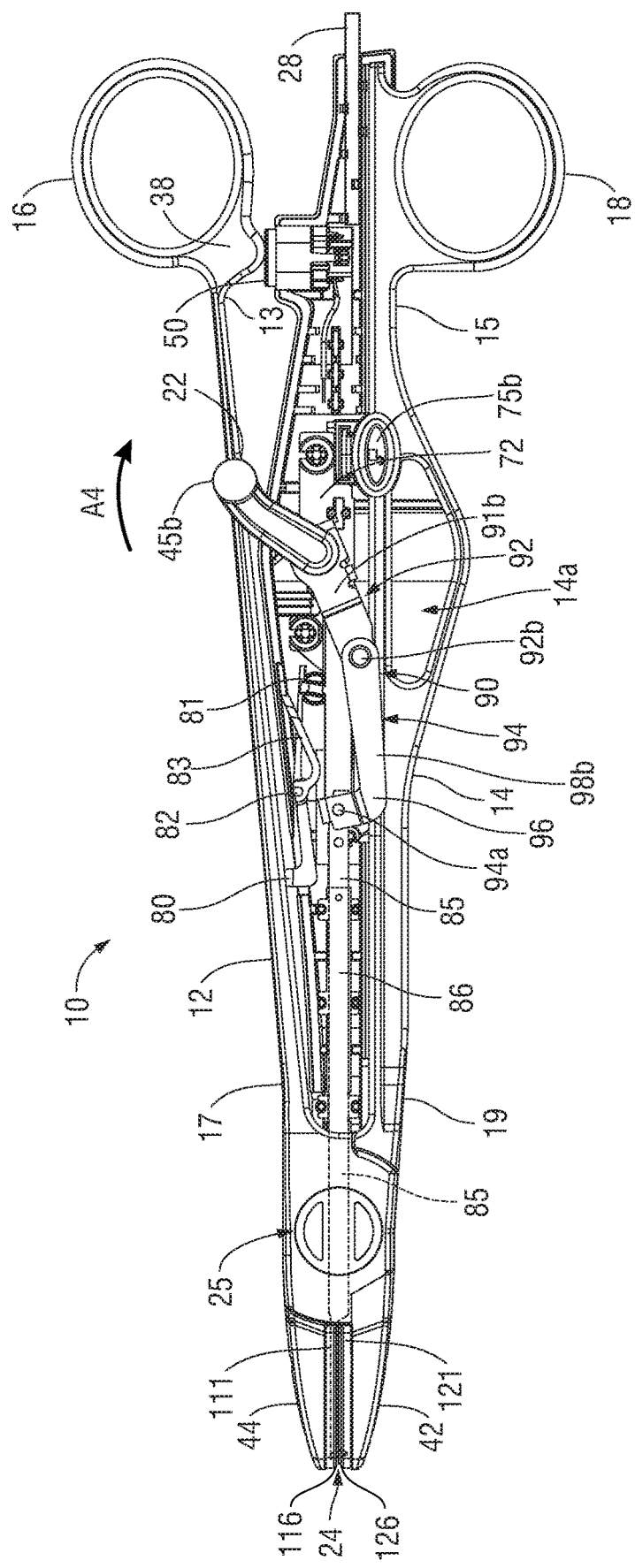

As shown in FIG. 1, housing 70 includes a longitudinal opening 70c that opposes shaft member 12 and exposes engagement member 80 such that upon approximation of the shaft members 12, 14 to move the jaw members 42, 44 to the closed position (FIG. 9B), engagement member 80 is engaged by shaft member 12. Pressure applied to engagement member 80 by shaft member 12 through approximation of shaft members 12, 14 induces counter clockwise rotation of engagement member 80 and biasing member 83 about pivot pin 82 (as depicted by rotational arrow A3 in FIG. 9B) such that biasing member 83 imparts a biasing force on an interior of housing 70 and safety link 81 rotates counter clockwise about pivot pin 82 out of engagement with arcuate portion 96 of second link 94 (FIG. 9B). Once safety link 81 is rotated out of engagement with arcuate portion 96 of second link 94, knife blade 85 is permitted to advance distally into the knife channel 58 (FIG. 9C). Operation of the knife actuation mechanism 90 and actuation of the knife blade 85 is further detailed below with reference to FIGS. 9A-9C.

The tissue seal thickness and tissue seal effectiveness may be influenced by the pressure applied to tissue between jaw members 44, 42 and the gap distance between the opposing electrodes 110 and 120 (FIG. 5) during tissue sealing. In the closed configuration, a separation or gap distance "G" may be maintained between the sealing surfaces 116, 126 by an array of stop members 54 (FIG. 2) disposed on one or both of sealing surfaces 116, 126 (only shown disposed on sealing surface 126 for purposes of illustration). The stop members 54 contact the sealing surface on the opposing jaw member and prohibit further approximation of the sealing surfaces 116, 126. In some embodiments, to provide an effective tissue seal, an appropriate gap distance of about 0.001 inches to about 0.010 inches and, desirably, between about 0.002 and about 0.005 inches may be provided. In some embodiments, the stop members 54 are constructed of an electrically non-conductive plastic or other material molded onto the sealing surfaces 116, 126, e.g., by a process such as overmolding or injection molding. In other embodiments, the stop members 54 are constructed of a heat-resistant ceramic deposited onto sealing surfaces 116, 126.

FIG. 8 shows the bipolar forceps 10 during use wherein the shaft members 12 and 14 are approximated to apply clamping force to tissue 150 and to effect a tissue seal. Once sealed, tissue 150 may be cut along the tissue seal through actuation of the knife blade 85, as detailed below with reference to FIG. 9C.

Referring now to FIGS. 9A, 9B, 9C, and 9D, a sequence of motions may be initiated by moving the shaft members 12, 14 in order to close the jaw members 42, 44, and by actuating the handle members 45a, 45b to induce the knife actuation mechanism 90 to translate the knife blade 85 through the knife channel 58. Initially, shaft members 12, 14 are in the open configuration and the handle members 45a, 45b are in an unactuated configuration as depicted in FIG. 9A. This arrangement of shaft members 12, 14 and handle members 45a, 45b sustains the end effector 24 in the open configuration wherein the jaw members 42, 44 are substantially spaced from one another, and the knife blade 85 is in an unactuated position with respect to the jaw members 42, 44. The unactuated configuration of the handle members 45a, 45b depicted in FIGS. 9A and 9B is actively maintained by the influence of the biasing member 95 on the trigger 45. When jaw members 42, 44 are in the open configuration, as depicted in FIG. 9A, safety link 81 is engaged with arcuate portion 96 of second link 94 such that rotational motion of the handle members 45a, 45b in a proximal direction (depicted by rotational arrow A4 in FIG. 9C) is prohibited so that knife blade 85 is prohibited from advancing into knife channel 58.

The jaw members 42, 44 may be moved from the open configuration of FIG. 9A to the closed configuration depicted in FIG. 9B. As the shaft members 12, 14 pivot about pivot 25 in the directions of arrows A1 and A2 (FIG. 9B), respectively, shaft member 12 engages engagement member 80 and button activation post 38 engages button 50. In some embodiments, shaft 12 engages engagement member 80 simultaneously with button activation post 38 engaging button 50. As the shaft members 12, 14 pivot further about pivot 25 in the directions of arrows A1 and A2, respectively, button activation post 38 depresses activation button 50 to initiate delivery of electrosurgical energy to end effector 24 and shaft 12 applies pressure on the engagement member 80. The pressure applied on engagement member 80 by shaft 12 induces rotation of engagement member 80 and biasing member 83 about pivot pin 82 in the direction depicted by rotational arrow A3 (FIG. 9B) such that biasing member 83 imparts a biasing force on an interior of housing 70 and safety link 81 rotates about pivot pin 82 in the direction depicted by rotational arrow A3 (FIG. 9B) out of engagement with arcuate portion 96 of second link 94, as shown in FIGS. 9B and 9C.

Upon movement of safety link 81 out of engagement with arcuate portion 96 of second link 94, handle members 45a, 45b may be selectively moved from the unactuated configuration of FIGS. 9A and 9B to the actuated configuration of FIG. 9C to advance the knife blade 85 distally through knife channel 58. More specifically, as handle members 45a, 45b rotate in the general proximal direction, as depicted by rotational arrow A4 in FIG. 9C, the first link 92 imparts a rotational force on second link 94, thereby causing second link 94 to rotate about pivot pin 94a and translate pivot pin 94a distally through longitudinal channel 76 to advance knife blade 85 distally into the knife channel 58.

Figure 9D:
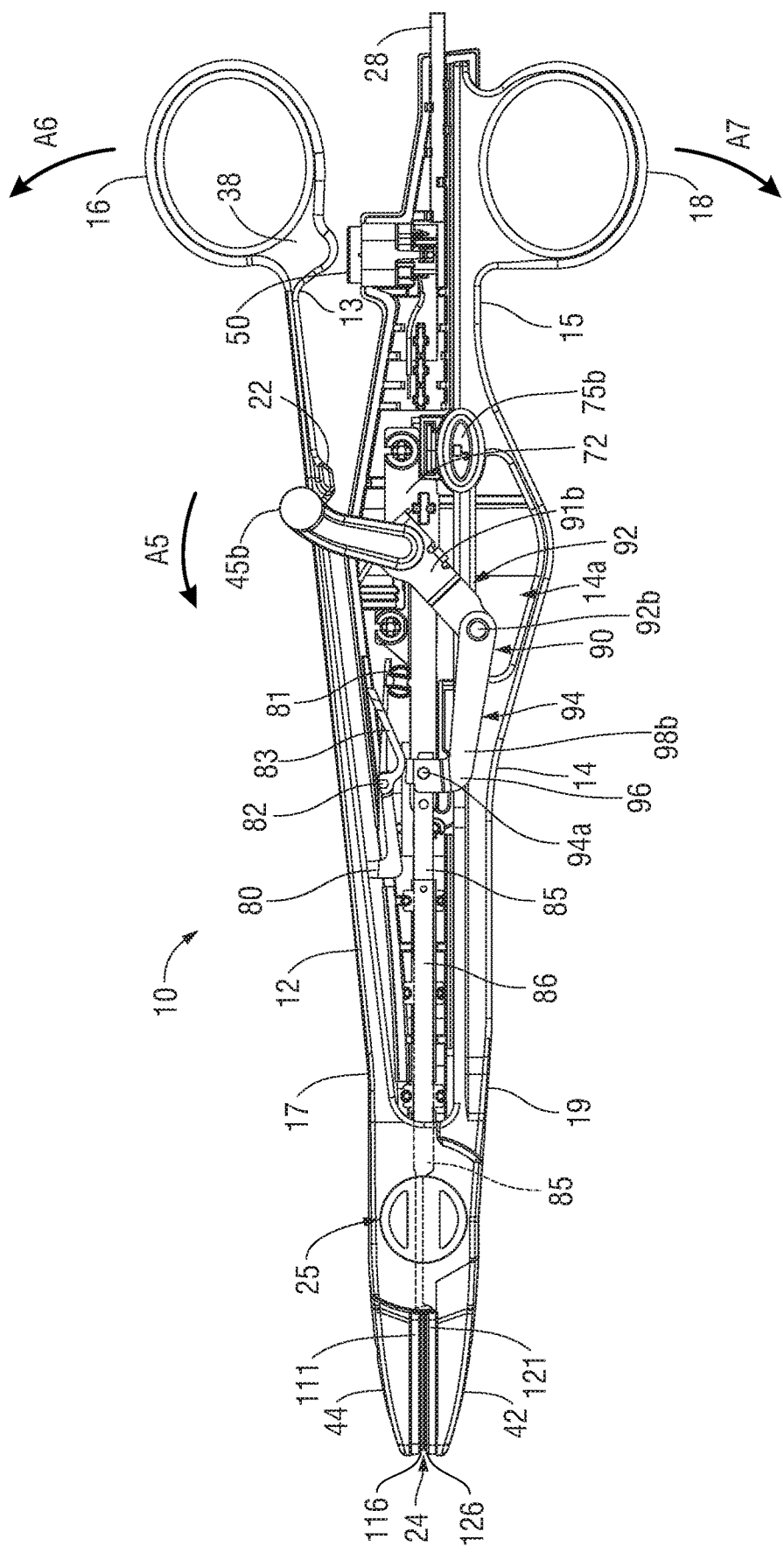

As indicated above, the initial position of the handles 45a, 45b depicted in FIGS. 9A and 9B is actively maintained by the influence of the biasing member 95 on the trigger 45. With reference to FIG. 9D, in the event that handles 45a, 45b fail to return to their initial position (FIGS. 9A and 9B) following movement to the actuated configuration (FIG. 9C), movement of the shaft members 12, 14 to the open configuration serves as a fail-safe to return handles 45a, 45b to the unactuated configuration (FIGS. 9A and 9B). More specifically, as shaft members 12, 14 move from the closed configuration toward the open configuration, depicted by arrows A6 and A7, respectively, knife kickback 22 engages handles 45a, 45b such that handles 45a, 45b are forced in the general distal direction, depicted by rotational arrow A5 in FIG. 9D, to the unactuated configuration depicted in FIGS. 9A and 9B.

Figure 10A:
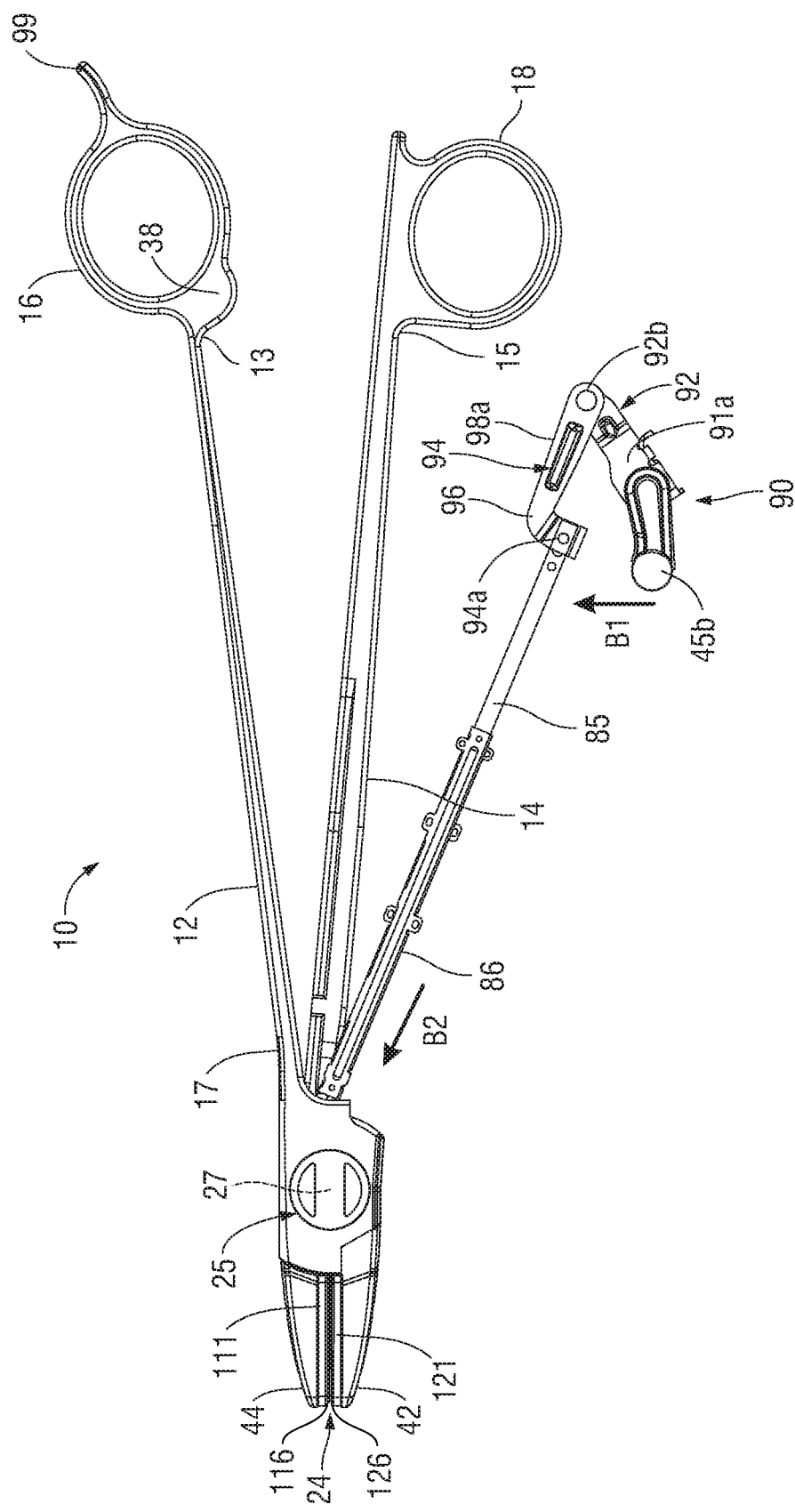
FIGS. 10A and 10B are generally internal, side views of a bipolar forceps according to another embodiment of the present disclosure with parts partially removed.
Figure 10B:
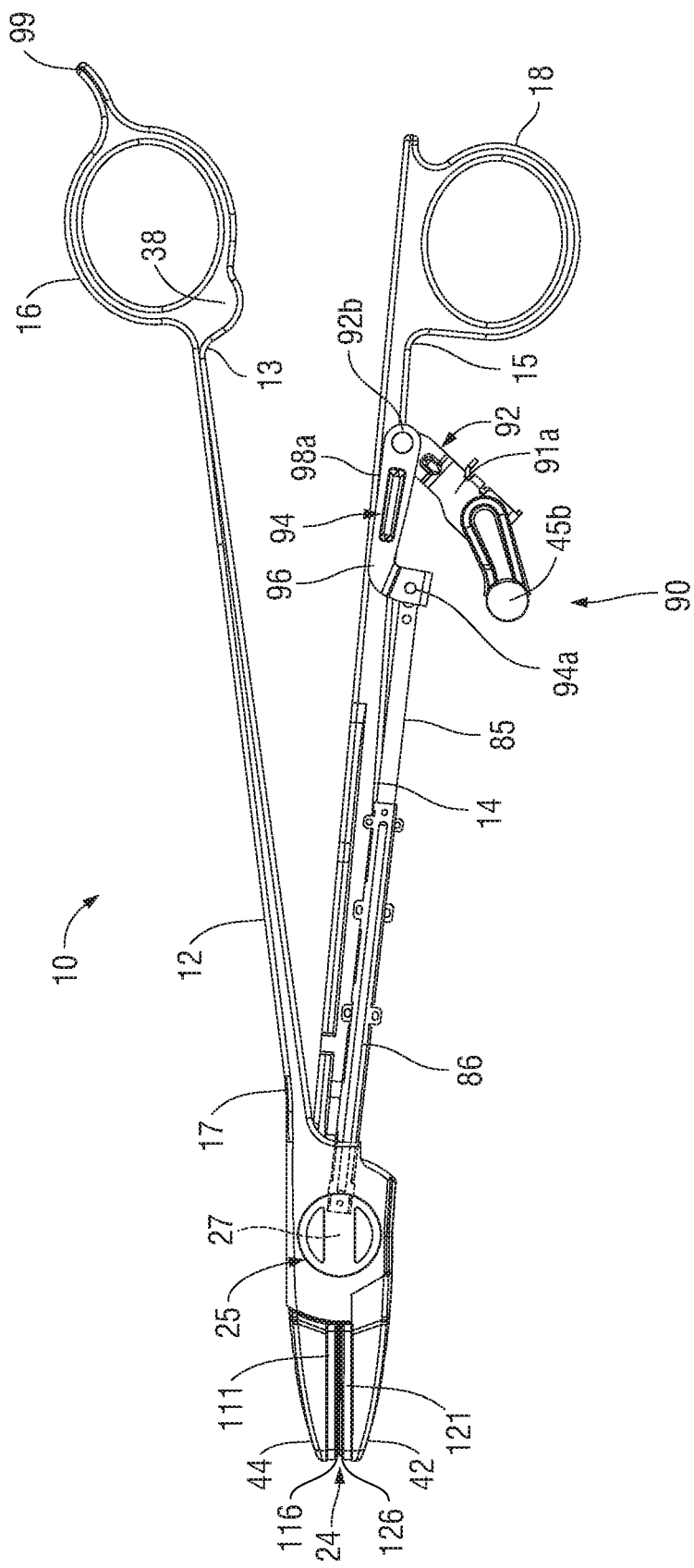

Referring now to FIGS. 10A and 10B, an alternative embodiment of forceps 10 is shown. Referring initially to FIG. 10A, shaft members 12, 14 are configured such that upon affixing of shaft members 12, 14 to each other about pivot 25, shaft member 14 is disposed at an angle relative to shaft member 12 that is substantially different than the angle depicted by the embodiment of FIGS. 9A-9D. This allows the knife 85, the knife guide 86, the knife actuation mechanism 90, and the trigger 45 to be assembled with the mechanical forceps 20 from an exterior side of shaft member 14 (e.g., from the side of shaft member 14 from which handle member 18 extends as opposed to an interior side of shaft member 14 that faces shaft member 12), as illustrated by FIGS. 10A and 10B. More specifically, during assembly of forceps 10, knife guide 86 may be inserted into passageway 27 of pivot 25 from an exterior side of shaft member 14, as depicted by directional arrow B2. As knife guide 86 is inserted into passageway 27, the knife actuation assembly 90 may be moved toward shaft member 14 and, upon suitable placement of knife actuation assembly 90 relative to shaft member 14, housing 70 (removed from FIGS. 10A and 10B for clarity) may be releasably coupled to shaft member 14 to at least partially house knife 85, knife guide 86, and knife actuation mechanism 90 substantially as described above with respect to FIGS. 2 and 3. The ability to assemble forceps 10 in the manner described above with respect to FIGS. 10A and 10B conveniently allows forceps 10 to be assembled in the sterile field and/or the operating theater before or during a medical procedure.

Figure 11A:
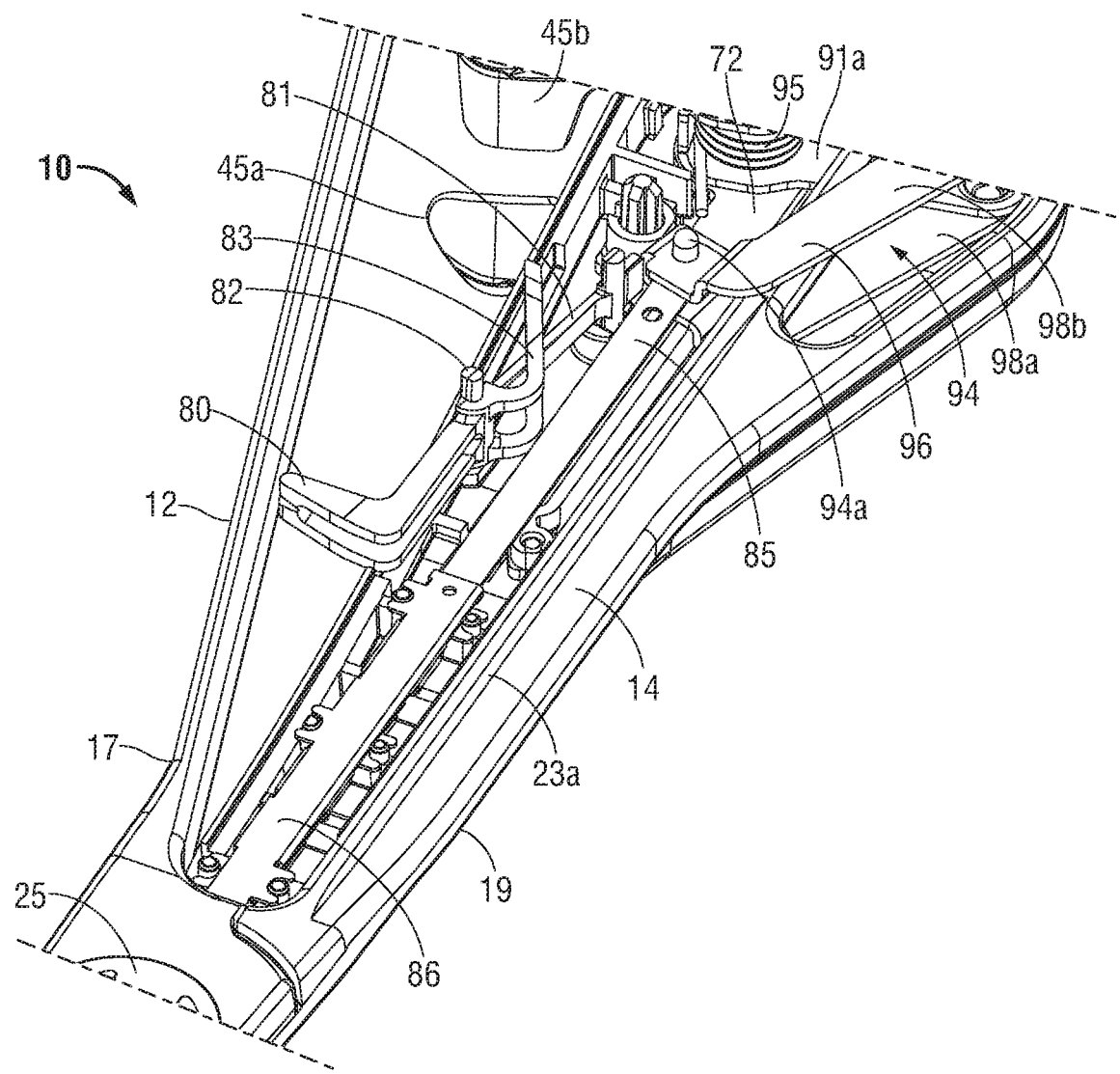
FIG. 11A is an enlarged, perspective view of a distal portion of a bipolar forceps according to another embodiment of the present disclosure with parts partially removed.
Figure 11B:
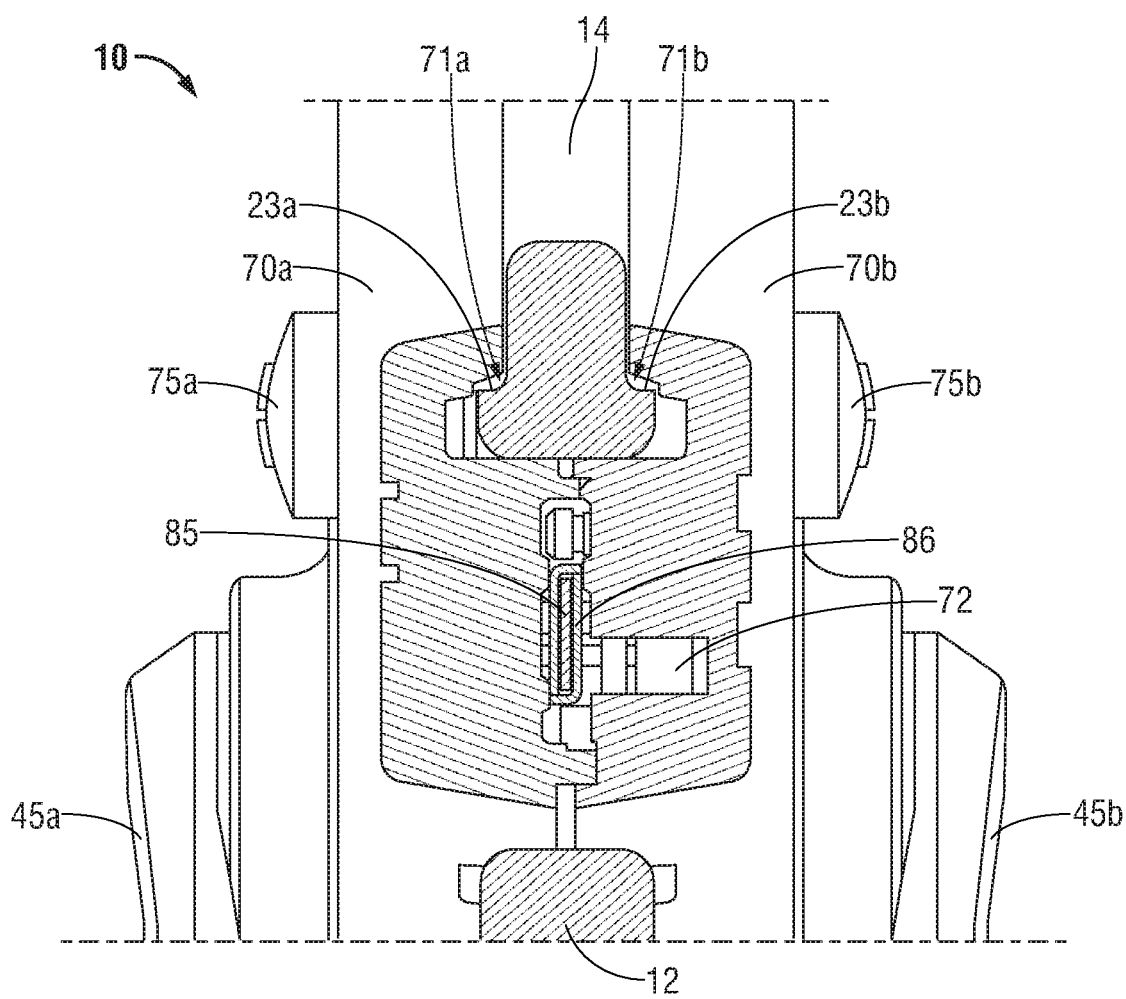
FIG. 11B is an enlarged, cross-sectional distal view of the bipolar forceps of FIG. 11A taken through a central portion of the bipolar forceps.

Referring now to FIGS. 11A and 11B, an alternative embodiment of forceps 10 is shown. In this embodiment, shaft member 14 forms a pair of opposing guide rails 23a, 23b extending along a distal portion thereof. When housing halves 70a, 70b are coupled, as shown in FIG. 11B, housing 70 forms a pair of opposing guide channels 71a, 71b that are configured to capture guide rails 23a, 23b therein, respectively. When coupling housing 70 to shaft member 14, housing 70 may be moved relative to shaft member 14 such that guide rails 23a, 23b slide within guide channels 71a, 71b, respectively, to ensure proper placement of housing 70 relative to shaft member 14. In some embodiments, guide rails 23a, 23b may be formed between approximately a middle portion of shaft member 14 to distal end 19 of shaft member 14. Guide channels 71, 71b may be aligned with a proximal end of guide rails 23a, 23b, respectively, at the middle portion of shaft member 14. Housing 70 may then be pushed distally along shaft member 14 so that guide rails 23a, 23b slide within guide channels 71a, 71b to ensure proper placement of housing 70 relative to shaft member 14.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A method of assembling an electrosurgical instrument including first and second shafts, a pivot, a knife blade, and a knife actuation mechanism, comprising:

coupling the first and second shafts to the pivot, the first shaft having an interior side facing the second shaft and an exterior side opposite the interior side;

coupling the knife actuation mechanism to the knife blade;

disposing the knife blade at least partially through a passageway defined through the pivot from the exterior side of the first shaft subsequent to coupling the knife actuation mechanism to the knife blade; and coupling the knife actuation mechanism to the first shaft from the exterior side of the first shaft subsequent to disposing the knife blade at least partially through the passageway, the knife actuation mechanism configured to move the knife blade through the passageway.

2. The method according to claim 1, further comprising releasably coupling a housing to the first shaft subsequent to coupling the knife actuation mechanism to the first shaft to house at least a portion of the knife actuation mechanism and at least a portion of the knife blade.

3. The method according to claim 1, further comprising releasably coupling an electrode to a jaw member disposed at a distal end of one of the first or second shafts subsequent to coupling the knife actuation mechanism to the first shaft.

4. The method according to claim 3, wherein releasably coupling the electrode to the jaw member includes inserting an anchor extending from the electrode into a socket disposed in the jaw member.

5. The method according to claim 1, wherein disposing the knife blade at least partially through the passageway includes disposing a knife guide at least partially through the passageway while the knife blade is disposed at least partially within the knife blade.

6. The method according to claim 1, wherein coupling the knife actuation mechanism to the first shaft from the exterior side of the first shaft includes disposing the first shaft between opposing portions of the knife actuation mechanism.

7. The method according to claim 1, further comprising coupling a rotatable trigger to the knife actuation mechanism, the trigger configured to cause movement of the knife blade through the passageway.

8. A method of assembling an electrosurgical instrument including first and second shafts, a pivot, a knife guide, and a knife actuation mechanism, comprising:
   coupling the first and second shafts to the pivot, the first shaft having an interior side facing the second shaft and an exterior side opposite the interior side;
   coupling the knife actuation mechanism to the knife guide;
   disposing the knife guide at least partially through a passageway defined through the pivot from the exterior side of the first shaft subsequent to coupling the knife actuation mechanism to the knife guide; and
   coupling the knife actuation mechanism to the first shaft from the exterior side of the first shaft while the knife guide is disposed at least partially through the passageway.

9. The method according to claim 8, further comprising releasably coupling a housing to the first shaft subsequent to coupling the knife actuation mechanism to the first shaft to house at least a portion of the knife actuation mechanism and at least a portion of the knife guide.

10. The method according to claim 8, further comprising:
    providing a knife blade;
    coupling the knife blade to the knife actuation mechanism;
    disposing the knife blade at least partially within the knife guide subsequent to disposing the knife guide at least partially through the passageway.

11. The method according to claim 8, further comprising releasably coupling an electrode to a jaw member disposed at a distal end of one of the first or second shafts subsequent to coupling the knife actuation mechanism to the first shaft.

12. A method of assembling an electrosurgical instrument including first and second shafts, a pivot, a knife blade, and a knife actuation mechanism, comprising:
    coupling the first and second shafts to the pivot, the first shaft having an interior side facing the second shaft and an exterior side opposite the interior side;
    disposing the knife blade through the pivot from the exterior side of the first shaft subsequent to coupling the first and second shafts to the pivot; and
    coupling the knife actuation mechanism to the first shaft from the exterior side of the first shaft subsequent to disposing the knife blade through the pivot, the knife actuation mechanism configured to move the knife blade through the pivot.

\* \* \* \* \*